US006967187B1

(12) United States Patent
Hamley

(10) Patent No.: US 6,967,187 B1
(45) Date of Patent: *Nov. 22, 2005

(54) FLORAL PRESERVATIVE AND AROMATHERAPY PRODUCT, APPARATUS AND METHOD

(76) Inventor: Robert J. Hamley, 663 Main St., Hunter, NY (US) 12442

( * ) Notice: Subject to any disclaimer, the term of this patent is extended or adjusted under 35 U.S.C. 154(b) by 0 days.

This patent is subject to a terminal disclaimer.

(21) Appl. No.: 10/111,894
(22) PCT Filed: Oct. 26, 2000
(86) PCT No.: PCT/US00/29472
§ 371 (c)(1), (2), (4) Date: Jan. 6, 2004
(87) PCT Pub. No.: WO01/30142
PCT Pub. Date: May 3, 2001

Related U.S. Application Data

(63) Continuation of application No. 09/428,205, filed on Oct. 27, 1999, now Pat. No. 6,258,748.

(51) Int. Cl.[7] .............................. A01N 3/02; A01N 3/04
(52) U.S. Cl. ...................... 504/114; 504/292; 504/299; 504/357
(58) Field of Search ......................... 504/114, 292, 299, 504/357

(56) References Cited

U.S. PATENT DOCUMENTS

| 116,375 A | * | 6/1871 | Vining ......................... 504/114 |
| 1,779,299 A | * | 10/1930 | Valentine .................... 504/114 |
| 3,791,839 A | | 2/1974 | Cushman et al. |
| 3,929,448 A | * | 12/1975 | Brantley ......................... 71/86 |
| 4,348,424 A | | 9/1982 | Consolazio et al. |
| 4,885,175 A | | 12/1989 | Zibell |
| 5,723,407 A | * | 3/1998 | Midou et al. ............... 504/115 |
| 5,834,074 A | | 11/1998 | Mikkola |
| 6,258,748 B1 | | 7/2001 | Hamley |

FOREIGN PATENT DOCUMENTS

GB 2189676 11/1987

OTHER PUBLICATIONS

Creekmore, Betsey B. Making Gifts from Oddments & Outdoor Materials. Hearthside Pr.: NY. p. 167-169.*

Database WPI, Section Ch, Week 199431, Derwent Publications Ltd., London, GB; Class E19, AN 1994-252656, XP002161255 & JP 06 183903 (Hyponex Japan KK), Jul. 5, 1994.

Database WPI, Section Ch, Week 199624, Derwent Publications Ltd., London, GB; Class A97, AN 1996-235893, XP002161256 & JP 08 092003 (Toppon Printing Co. Ltd.), Apr. 9, 1996.

* cited by examiner

*Primary Examiner*—S. Mark Clardy
(74) *Attorney, Agent, or Firm*—Jay R. Yablon

(57) ABSTRACT

To preserve flowers (6) and provide aromatherapy, low temperature paraffin (1) is heated (2) to a liquid state of approximately 130 degrees Fahrenheit. A floral nutrient and preservative (3) such as a saccharide such as sugar is then added to the low temperature paraffin (1). Optionally, scents (4) and/or color dyes (5) are also added. The heads of flowers (6) to be preserved are then dipped (7) in this paraffin mixture for one to three seconds and thereafter allowed to dry. The flower (6) can then be used immediately, or optionally hung (8) upside down for one to three weeks prior to use to further improved shelf life. The flower (6) can further be sprayed with a floral spray paint (9).

22 Claims, 1 Drawing Sheet

FLORAL PRESERVATIVE AND AROMATHERAPY PRODUCT, APPARATUS AND METHOD

This application has been filed under 35 USC 371 as the U.S. national stage application of PCT/US00/29472 filed Oct. 26, 2000, which is a continuation of U.S. application Ser. No. 09/428,205 filed Oct. 27, 1999, now U.S. Pat. No. 6,258,748 issued Jul. 10, 2001.

FIELD OF THE INVENTION

This invention relates to the field of floral preservatives, and specifically, to a device and method used to preserve cut flowers well beyond their ordinary shelf life.

BACKGROUND OF THE INVENTION

Flowers have long been a special gift for birthdays, anniversaries, weddings, and many other special occasions. However, the gift of flowers only lasts for a short time. Within a few short days or weeks, cut flowers wilt and die unless they have been properly preserved.

Over time, various approaches to preserving flowers have been developed. These include freeze drying, hang drying, use of silica gels and sand mixtures, and spraying with the various compounds such as polyurethane, hairspray, and shellac. However, none of these approaches is fully satisfactory in terms of the shelf life achieved, the ability to achieve a lasting, pleasant aroma, and/or providing suitable coloration.

Additionally, desired scents and colorations, if any, are frequently introduced after the flower has already been preserved, rather than during the preservation process itself, which makes these susceptible to wearing off over time.

U.S. Pat. No. 5,723,407 observes that "[t]o avoid full exhaustion of nutrients in cut flowers, it is known that a saccharide such as sugar is added to vase water. The effects of these additives can however be varying and are not always attainable to a noticeable extent." (column 2, lines 5–8). This patent goes on to disclose a sulfonylsemicarbazide derivative composition for preserving the cut flower freshness of the general formula:

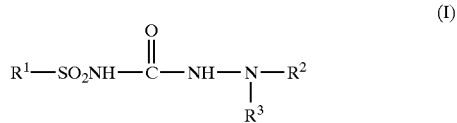

(I)

Thereafter, in column 12, lines 52–61, this patent states that, in reference to the compound (I), "[a]djuvants such as . . . saccharides . . . may be incorporated therein further, as needed. Further, the composition . . . can also be formulated by mixing and diluting the compound of the general formula (I) appropriately with a solid carrier, for example . . . a saccharide."

Thus, while a saccharide such as sugar is stated to be a suitable adjuvant (i.e., a helping or supplementary agent) to the composition (I), this patent does not disclose or suggest that a saccharide such as sugar might be fully capable of preserving flowers all by itself, and without combination with a further chemical composition such as (I). Indeed, the statement that "the effects of these additives can however be varying and are not always attainable to a noticeable extent" teaches clearly away from using a saccharide such as sugar all by itself and omitting any other preserving agent such as (I). Similarly, the entire thrust of this patent, which focuses throughout on synthesizing and using many different variations of the compound (I), makes clear that the compound of the general formula (I) is the "effective ingredient" (column 12, line 41), and that a saccharide such as sugar is merely an adjuvant. Nowhere does this patent disclose or suggest that a saccharide itself can work well as the sole "effective ingredient" for floral preservation. Nowhere is it disclosed or suggested that flowers can be similarly preserved by omitting the specialized compound (I), which is much less widely-available than sugar, and which is likely much more expensive.

U.S. Pat. No. 4,885,175 teaches a method of making chewing gum by first mixing powdered "high-potency" (i.e., non-nutritive: col 3, lines 15–65) sweeteners, flavors, and/or acidulants with molten (at 130° C.) wax to make wax coated particles which are then incorporated into a chewing gum formulation (claim 1). While sugar is discussed (line 64) as a bulking agent which may be added to the sweeteners, there is no suggestion or teaching to use saccharides alone in the intermediate wax compositions in this non-analogous art reference.

U.S. Pat. No. 5,834,074 teaches preservation of dried flowers by treatment with an aqueous composition comprising a sugar based syrup (corn syrup) and detergent. There is no suggestion or teaching of replacing the detergent component with wax. GB 2,189,676 teaches the utility of a sugar constituent in combination with several other agents in cut flower preservation compositions. The utility of sugar alone as an active preservative and nutrient component is not suggested or taught. JP 6,183,903 discloses only that a "forming tablet for life prolongation of a cut flower is characterized by containing a life prolongation component and a foaming component composed of a carbonate and a water-soluble solid acid." (see Patent Abstracts of Japan for JP 6,183,903)

JP 8,092,003 teaches the utility of coating cut flowers with a membrane forming composition which is preferably a water soluble polymer. Substitution of wax for the polymer, and further inclusion of a saccharide component is not suggested or taught. U.S. Pat. No. 3,791,839 teaches using wax compounds to avoid transpiration in plants, but nowhere does it disclose or suggest a combination with any form of saccharide or other nutrient. U.S. Pat. No. 4,348,424 teaches using orange peel wax, and a number of non-saccharide nutrients and preservatives. Use or substitution of a saccharide component, or of a saccharide component alone, is not suggested or taught.

While these references individually teach cut flower preservative compositions comprising wax or other coating materials in combination with nutritive and other agents such as bactericides and scents, no reference discloses or suggests limiting cut flower preserving compositions to low temperature wax and a saccharide component.

Additionally, none of these references disclose or suggest that if sugar or similar saccharides are mixed with paraffin, and if this mix is then used to coat the head of a flower, formaldehyde contained within this sugar or similar saccharides will be released from the paraffin mix over time, serving not only to feed the flower, but also to preserve/mummify the flower.

It is desirable, therefore, to provide an improved device and method for preserving flowers which increases their shelf life substantially.

It is further desirable to integrate such an improved device and method for preserving flowers with an improved device and method to provide a lasting, pleasant aroma, and/or the ability to provide suitable coloration to the preserved flowers.

SUMMARY OF THE INVENTION

Low temperature paraffin is heated to a liquid state of approximately 130 degrees Fahrenheit. A floral nutrient and preservative such as a saccharide such as sugar is then added to the low temperature paraffin. Optionally, scents and/or color dyes are also added. The heads of the flowers to be preserved are then dipped in this paraffin mixture for one to three seconds and thereafter allowed to dry. The flower can then be used immediately, or optionally hung upside down for one to three weeks prior to use to further improve shelf life. The flower can further be sprayed with a floral spray paint.

BRIEF DESCRIPTION OF THE DRAWING

The features of the invention believed to be novel are set forth in the appended claims. The invention, however, together with further objects and advantages thereof, may best be understood by reference to the following description taken in conjunction with the accompanying drawing in which:

DETAILED DESCRIPTION OF THE INVENTION

Figure 1:
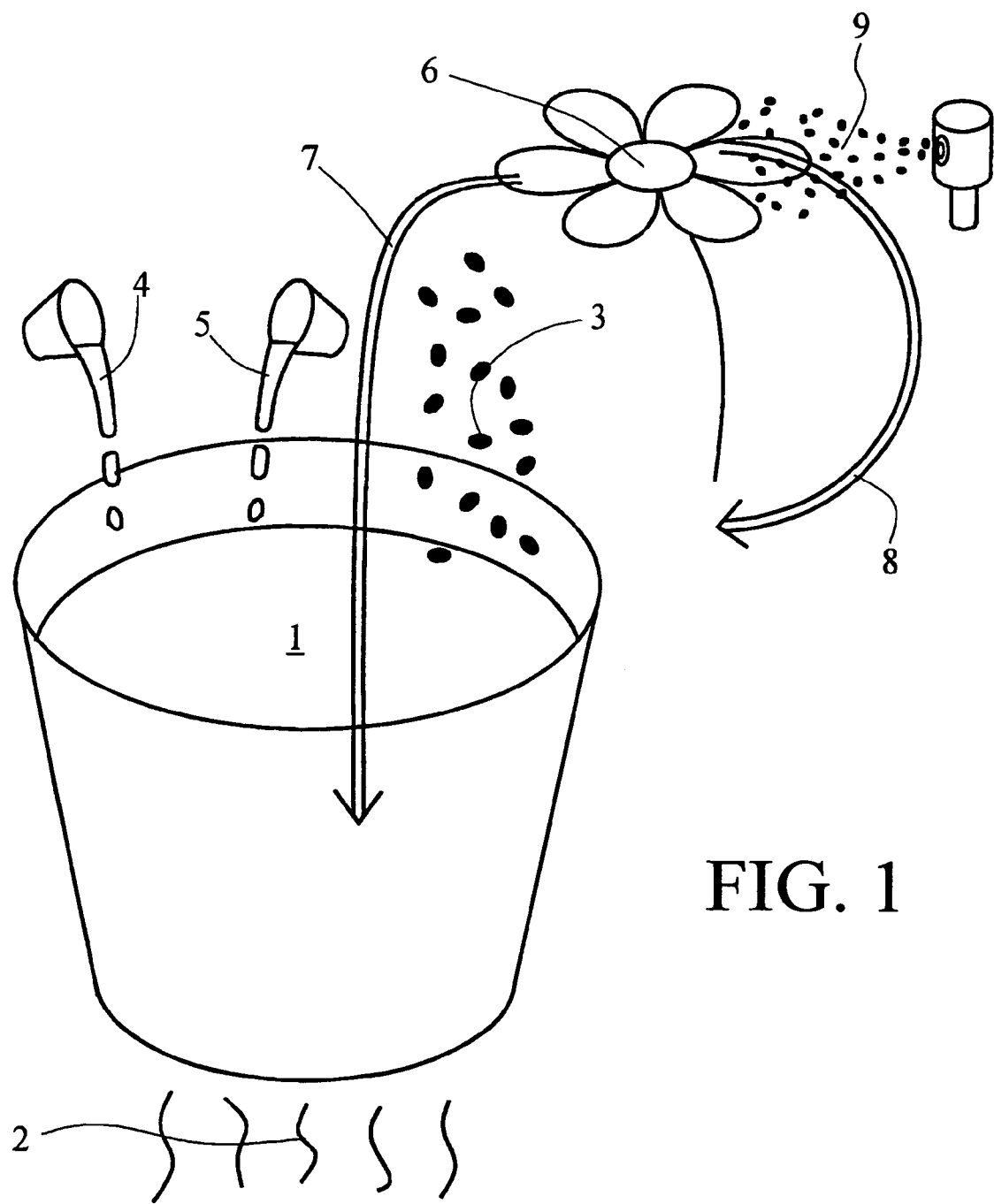
FIG. 1 is a schematic view illustrating the apparatus and method through which the paraffin mix used to preserve flowers is prepared and used in the preferred embodiment of the invention.

Low temperature paraffin 1 is first heated 2 to a liquid state of approximately 130 degrees Fahrenheit. In a preferred embodiment, low temperature paraffin 1 is a member of the petroleum hydrocarbon family, and is preferably a petroleum paraffin wax. It is preferred that low temperature paraffin 1 be highly refined so as to comprise long chain saturated hydrocarbon molecules.

Next, a floral nutrient and preservative 3 is mixed into low temperature paraffin 1. In a preferred embodiment, floral nutrient and preservative 3 comprises a saccharide such as sugar, preferably white granulated or liquid sugar. Approximately one pinch of floral nutrient and preservative 3 is added for each pound of low-temperature paraffin 1. In alternative embodiment of the invention, floral nutrient and preservative 3 may comprise, alternatively or in addition to sugar, one or more of honey, saccharin, aspartame, or any other known sweetener.

Next, for each pound of low-temperature paraffin 1, approximately ½ ounce of scent 4 is added. Scent 4 can be a floral or a non-floral scent, and is generally in a liquid form but may also be in a powder of other solid form as well within the scope of this disclosure and its associated claims. Scent 4 may comprise, but is not limited to, one or more of: jasmine, rose, lavender, petitgrain, patchouli, juniper, ginger, orange blossom, tangerine, rosemary, peppermint, peach blossom, eucalyptus, lemon, balsam fir, bergamot, ylang, neroli, sandalwood, chamomile, germanium, musk, frankincense, cedar, plum, mandarin, pine, tea tree, clary sage, vetiver, cypress, coriander, lemon, grapefruit, bergamot, cordamon, basil, lilac, everlasting, lily, lily of the valley, and any and all other known scents.

Optionally, if coloration is desired, approximately 1/24 gram of a colored dye 5 for whatever color is desired is then added, for each pound of low-temperature paraffin 1. Dye 5 is also typically a liquid, but can also be a powder or similar solid formulations as well within the scope of this disclosure and its associated claims.

Finally, the flower 6 head only, is dipped 7 into the above paraffin mixture comprising low-temperature paraffin 1 and any or all of floral nutrient and preservative 3, scent 4, and dye 5, for a predetermined dip time of approximately one to three seconds. Then, flower 6 is used for decorative purposes and/or for aromatherapy, as desired. A single, short dip 7 such as described above coats the flower lightly with the paraffin mix and keeps the flower looking more natural and alive. Longer, and/or multiple dips, would cause the flower to appear heavy and waxy, and would diminish shelf life.

Optionally, prior to use, to bring about an even longer shelf life, flower 6 may be hung upside down 8 for a predetermined hang time of approximately one to three weeks, or until the stem becomes hard like a stick. This strengthens the flower stem and enables it to better support the weight of the paraffin mixture on the flower 6 head. Floral nutrient and preservative 3 is particularly important, since it adds a great deal of shelf life to preserved flower 6 over what is achieved by dipping in low temperature paraffin 1 alone. In particular, formaldehyde contained within sugar and similar saccharide embodiments of floral nutrient and preservative 3 is released from the paraffin mix over time, so that floral nutrient and preservative 3 not only feeds flower 6, but also acts to preserve/mummify it. From a functional standpoint, this means that any nutrient which feeds flower 6 over time and also releases formaldehyde or a similar preservative compound over time is suitable for use as floral nutrient and preservative 3.

Scent 4 allows flower 6 to emit a pleasing aroma long after flower 6 has been preserved, and enables flower 6 to be used for aromatherapy and related purposes.

It is also possible, for aromatherapy, maintain the paraffin mix comprising low temperature paraffin 1 and scent 4 in a heated, liquid state, whether or not a flower is dipped into it. Aroma from this mix then wafts into the surrounding environment, again, providing a pleasing aroma.

After flower 6 has been dipped 7, dried, and optionally hung 8, flower 6 may optionally by sprayed with a floral spray paint 9. This adds more shine to flower 6, and keeps the color more vibrant and realistic-looking over time.

It is to be understood that for commercial purposes, it may be desirable to prepare the entire paraffin mixture in a mass-production setting, cool the paraffin mixture into a portable solid, and then distribute this cooled, solid paraffin mixture to the end user in tubs or similar containers. These tubs, and the solid paraffin mixture they contain, would then be slowly heated by the end user to approximately 130 degrees and liquefied as noted above. This slow heating can utilize any of the means known in the art for such a purpose. For example, it can be heated in a double-boiler, where the temperature of the heated water is maintained below about 160 degrees Fahrenheit; or in a crock pot with a suitable controlled temperature. The low (130 degrees) temperature (and quick dip) is important for a number of reasons, including that this minimizes possible adverse impacts of heat on the flower itself. Flowers 6 are then dipped 7 into this heated liquid paraffin mixture as outlined above.

It is to be understood that the invention disclosed and claimed herein includes all of: the paraffin mixture disclosed herein (flower preservative product/composition of matter); the method by which this paraffin mixture is produced (method of manufacturing flower preservative product); the method by which the flowers are preserved using this paraffin mixture (flower preservative process); and preserved flowers which are themselves produced by this flower preserving process (preserved flower products by flower preservative process).

It is important to observe that the floral nutrient and preservative 3 consists only of a saccharide such as sugar and of no other nutrifying and preserving substances such as the chemical composition (I) of U.S. Pat. No. 5,723,407. In other words, it is important to observe that one or more saccharides such as sugar, by themselves, mixed in with the paraffin, are sufficient to preserve a flower 6, and that these saccharides need not be mixed together with any other nutrifying or preserving chemical substance such as (I) to achieve the floral preserving benefits of this invention. In short, it is possible to entirely omit any other nutrifying or preserving agent, and particularly agents which are far less-available and more expensive than saccharides. This is not at all disclosed or suggested by U.S. Pat. No. 5,723,407.

While only certain preferred features of the invention have been illustrated and described, many modifications and changes will occur to those skilled in the art. It is, therefore, to be understood that the appended claims are intended to cover all such modifications and changes as fall within the true spirit of the invention.

I claim:

1. A floral preservative, comprising:
   liquid paraffin; and
   a floral nutrient and preservative consisting only of at least one saccharide, mixed into said liquid paraffin.
2. The floral preservative of claim 1, further comprising:
   at least one scent mixed into said liquid paraffin.
3. The floral preservative of claim 1, further comprising:
   at least one colored dye mixed into said liquid paraffin.
4. The floral preservative of claim 2, further comprising:
   at least one colored dye mixed into said liquid paraffin.
5. A method of manufacturing a floral preservative, comprising the steps of:
   providing paraffin in a liquid state; and
   mixing a floral nutrient and preservative consisting only of at least one saccharide, into the liquid paraffin.
6. The manufacturing method of claim 5, further comprising the steps of:
   mixing at least one scent into said liquid paraffin.
7. The manufacturing method of claim 5, further comprising the steps of:
   mixing at least one colored dye into said liquid paraffin.
8. The manufacturing method of claim 6, further comprising the steps of:
   mixing at least one colored dye into said liquid paraffin.
9. A method of preserving flowers, comprising the steps of:
   applying a floral preservative to at least a head of a flower, said floral preservative comprising:
   liquid paraffin; and
   a floral nutrient and preservative consisting only of at least one saccharide, mixed into said liquid paraffin.
10. The method of claim 9, said floral preservative further comprising:
    at least one scent mixed into said liquid paraffin.
11. The method of claim 9, said floral preservative further comprising:
    at least one colored dye mixed into said liquid paraffin.
12. The method of claim 10, said floral preservative further comprising:
    at least one colored dye mixed into said liquid paraffin.
13. The method of claim 9, comprising the further step of:
    hanging said flower upside down for a predetermined hang time subsequent to said applying, thereby hardening a stem of said flower.
14. The method of claim 9, comprising the further step of:
    spraying said flower with a floral spray paint.
15. A preserved flower produced by a method of producing preserved flowers, said method comprising the steps of:
    applying a floral preservative to a head of said flower, said floral preservative comprising:
    liquid paraffin; and
    a floral nutrient and preservative consisting only of at least one saccharide, mixed into said liquid paraffin.
16. The preserved flower of claim 15, said floral preservative further comprising:
    at least one scent mixed into said liquid paraffin.
17. The preserved flower of claim 15, said floral preservative further comprising:
    at least one colored dye mixed into said liquid paraffin.
18. The preserved flower of claim 16, said floral preservative further comprising:
    at least one colored dye mixed into said liquid paraffin.
19. The preserved flower of claim 15, said method of producing preserved flowers comprising the further step of:
    hanging said flower upside down for a predetermined hang time subsequent to said applying, thereby hardening a stem of said flower.
20. The preserved flower of claim 15, said method of producing said preserved flowers comprising the further step of:
    spraying said flower with a floral spray paint.
21. The method of claim 9, said step of applying comprising dipping said at least said head of said flower into said floral preservative.
22. The preserved flower of claim 15, said step of applying comprising dipping said at least said head of said flower into said floral preservative.

* * * * *